(12) United States Patent
Sundstrom et al.

(10) Patent No.: US 6,797,699 B1
(45) Date of Patent: Sep. 28, 2004

(54) NEUROPROTECTIVE AGENTS

(75) Inventors: Lars Eric Sundstrom, Hampshire (GB); Fausto Iannotti, Hampshire (GB); Mark Bradley, Hampshire (GB); Ashley Ker Pringle, Hampshire (GB)

(73) Assignee: University of Southampton, Hampshire (GB)

( * ) Notice: Subject to any disclaimer, the term of this patent is extended or adjusted under 35 U.S.C. 154(b) by 0 days.

(21) Appl. No.: 09/581,397

(22) PCT Filed: Dec. 16, 1998

(86) PCT No.: PCT/GB98/03775
§ 371 (c)(1),
(2), (4) Date: Oct. 2, 2000

(87) PCT Pub. No.: WO99/31049
PCT Pub. Date: Jun. 24, 1999

(30) Foreign Application Priority Data

Dec. 16, 1997 (GB) .............................. 9726569

(51) Int. Cl.$^7$ ................................. C07K 5/06
(52) U.S. Cl. ................. 514/19; 530/331; 514/20; 562/560; 562/562
(58) Field of Search ............. 514/19, 20; 530/331; 562/560, 562

(56) References Cited

U.S. PATENT DOCUMENTS

| | | | | |
|---|---|---|---|---|
| 2,465,303 A | * | 3/1949 | Williams | ............... 549/319 |
| 4,956,504 A | * | 9/1990 | Takeuchi et al. | ............... 564/153 |
| 5,242,947 A | | 9/1993 | Cherksey et al. | ............... 514/628 |
| 5,432,202 A | | 7/1995 | Cherksey et al. | ............... 514/626 |
| 6,262,125 B1 | * | 7/2001 | Bergeron, Jr. | ............... 514/674 |

FOREIGN PATENT DOCUMENTS

| WO | WO91/00853 | 1/1991 |
|---|---|---|
| WO | WO93/12777 | 7/1993 |

OTHER PUBLICATIONS

Bodansky (Int J Pept Prot Res 25, 449–474, 1985).*
Aldrich Catalog, p. 102, 1992–1993 edition.*
Eldefrawi (Proc. Natl. Acad. Sci. U. S. A. 85(13), 4910–13, 1988).*
Hashimoto (Tetrahedron Lett. 28(30), 3511–14, 1987).*
Stiller (J. Am. Chemical. Soc. 62, 1779–1784, 1940).*
Stiller (J. Am. Chemical. Soc. 62, 1785–1790, 1940).*

* cited by examiner

*Primary Examiner*—Christopher S. F. Low
*Assistant Examiner*—David Lukton
(74) *Attorney, Agent, or Firm*—Price, Heneveld, Cooper, DeWitt & Litton

(57) ABSTRACT

Compounds of formula (I) wherein: Q represents an amidino group, a cyano group or a group of formula XYN—, (where X and Y are hydrogen or various groups); $R^a$ represents alkylene; $R^b$ and $R^c$ each represents alkylene, the total number of carbon atoms in said straight chains of $R^b$ and $R^c$ being 7); $R^2$ and $R^3$ each represents hydrogen, or a group of formula R, RCO—, ROCO—, or RNHCO—, where R represents alkyl or aryl; the chiral carbon atom indicated by the asterisk is in the L configuration; Z is an aromatic amino acid residue; n is 0 or 1; $R^1$ represents hydrogen, alkyl or aryl; and W represents hydrogen, alkyl or aryl; and pharmaceutically acceptable salts thereof have the ability to protect against the neuronal damage which may be caused by an ischemic event.

13 Claims, No Drawings

NEUROPROTECTIVE AGENTS

This application is a 371 of PCT/GB98/03775, filed Dec. 16, 1998 which claims priority to GB 9726569.8, filed Dec. 16, 1997.

The present invention relates to neuroprotective agents.

In events such as prolonged hypoxia and ischaemia, which may or may not be associated with hypoglycaemia, neuronal damage, to varying degrees, is encountered.

Ischaemia typically occurs during heart attacks, but the damage incurred at these times is substantially limited to the heart tissues, and certain treatments have been developed. With regard to the present invention, we are concerned with the effects of more long term ischaemia on the brain, such as occurs with stroke patients or as a result of head injury. The severity of the ischaemia depends on the nature of the stroke or injury, but, invariably, there is brain damages and it is this which the present invention addresses.

Various neuroprotective agents are known in the art which attempt to alleviate the problem of brain damage, but all of those currently known tend to be associated with adverse side effects. For example, MK801 (dizocilpine maleate) is a fairly simple molecule and is known to provide a level of neuroprotection to ischaemic patients. However, MK801 is also associated with "alarming psychotropic effects" (Martindale), as well as adverse motor effects. The neuroprotective effects are detailed in Brain Research 755 (1997) 36–46 (Pringle, A. K., et al), incorporated herein by reference. These same authors also described the neuroprotective effects of conotoxin in an earlier paper but, despite the neuroprotective effects of this compound, adverse side effects, in vivo, are observed.

Recently, research has been performed on a series of polyamine compounds related to spermidine, and these compounds are disclosed in WO93/12777, with specific reference to their use as cationic channel regulating agents. These compounds are disclosed in connection with methods for regulating cation transport across cellular membranes possessing cation channels, the compounds being polyamine compounds having a lysine or arginine-based moiety (or a guanidine moiety) coupled to a straight chain polyamine. Mention of their effect on NMDA N-methyl-D-aspartate) receptors is also made. These compounds were unpredictable in their effect on cationic channels, various compounds having an effect on P-type calcium channels, whilst other compounds had effects on potassium and sodium channels. Although these compounds have subsequently been used in research for their effects on calcium channels, research effectively finished with the publication in Proc. Natl. Acad. Sci. USA [86, 1689–1693 (1989), Llinàs, R, et al], which disclosed that a substance known as FTX from funnel-web spider toxin was toxic to mice in extremely small doses.

The present inventors were not aware of the research by Llinàs and his colleagues, and were pursuing similar compounds, as they were known to have some calcium channel blocking activity. In fact, what was discovered was that, not only is the calcium channel blocking activity not very significant, but also there is little or no effect on NMDA receptors. Further, it was also established that these compounds are, despite the earlier research, non-toxic, and they also have a substantial neuroprotective effect.

It is believed that the reason for the discrepancy between the earlier results and the present results lies in the preparation of the compounds. In particular, the FTX component of funnel-web spider toxin was specifically isolated from the toxin in the prior art, rather than being prepared separately.

This compound is currently thought to have the following formula (1)

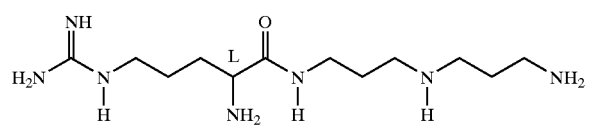

Related compounds have been manufactured synthetically, using the approaches described herein, which result in little or no detectable contamination of the end product. The results in the various assays have, therefore, been exceedingly surprising in that the compounds have proven non-toxic, as well as to have little effect on calcium channels. Indeed, if there were a substantial effect on P-type calcium channels and/or the compounds were toxic, then there would be no use for them in the clinical field. Instead, we find that the compounds, in their purified form, have use as neuroprotective agents.

Thus, in a first aspect, the present invention provides a substantially pure compound having the general formula (I)

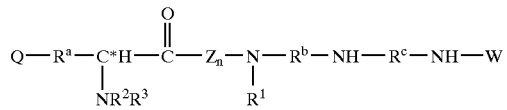

wherein:

Q represents an amidino group, a cyano group or a group of formula XYN—, where
X and Y are the same or different, and each may represent a hydrogen atom, a lower alkyl group, or a simple hetero-atom containing group or, together with the nitrogen atom to which they are attached, form a nitrogen-containing heterocyclic group;

$R^a$ represents a straight or branched chain alkylene or alkenylene group having from 1 to 6 carbon atoms and each optionally being substituted by from 1 to 4 alkyl groups each having from 1 to 3 carbon atoms;

$R^b$ and $R^c$ each represents an alkylene or alkenylene group having 3 or 4 carbon atoms in a straight chain, each being optionally substituted by 1 or 2 alkyl groups each having from 1 to 3 carbon atoms, the total number of carbon atoms in said straight chains of $R^b$ and $R^c$ being 7;

$R^2$ and $R^3$ are the same as or different from each other and each represents a hydrogen atom, or a group of formula R, RCO, ROCO—, or RNHCO—, where
R represents a lower alkyl group or an aryl group, said alkyl or aryl group being optionally substituted by one or more of the substituents α, defined below;

the chiral carbon atom indicated by the asterisk is in the L configuration;

Z is an aromatic amino acid residue;

n is 0 or 1;

$R^1$ represents a hydrogen atom or a lower alkyl group or an aryl group, said alkyl or aryl group being optionally substituted by one or more of the substituents α, defined below; and W represents a hydrogen atom or an alkyl or aryl group;

and pharmaceutically acceptable salts thereof.

A preferred class of compounds of the present invention are those compounds of formula (Ia):

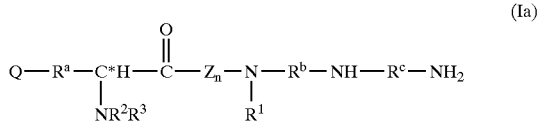

(wherein Q, $R^a$, $R^b$, $R^c$, $R^2$, $R^3$, Z, n, and $R^1$ are as defined above) and pharmaceutically acceptable salts thereof.

A still more preferred class of compounds of the present invention are those compounds of formula (Ib):

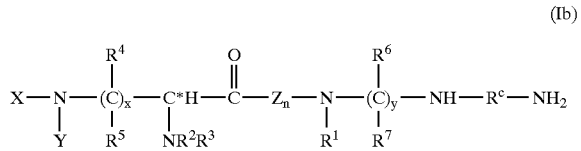

wherein:
X, Y, Z, n and $R^1$ are as defined above;
x is an integer from 1 to 5;
y is 3 or 4
$R^4$, $R^5$, $R^6$ and $R^7$ may be the same or different and each represents a hydrogen atom or a lower alkyl group; and the chiral carbon atom indicated by the asterisk is in the L configuration;
and pharmaceutically acceptable salts thereof.

Substituents α are selected from: halogen atoms, amino groups, alkylamino groups, dialkylamino groups, cyano groups, hydroxy groups, alkyl groups (except when the substituted group is alkyl), aryl groups, carbamoyl groups, alkylcarbamoyl groups, dialkylcarbamoyl groups and carboxy groups and esters thereof.

The present invention further provides non-toxic compounds of formula (I), (Ia) or (Ib) as defined above. There is still further provided a neuroprotective composition comprising a compound as defined above, as well as use of a compound as defined above in the manufacture of a medicament for the retardation of neuronal damage before, after or during an ischaemic event. The invention also provides a method of treating a mammal, which may be human, to protect said mammal from the neuronal damage caused by an ischaemic event by administering to said mammal before, after or during an ischaemic event an effective amount of a non-toxic compound of formula (I), (Ia) or (Ib) as defined above.

By substantially pure is meant a compound which, under conditions of HPLC (high performance liquid chromatography) is not shown to have any or any significant amount of contaminants detectable thereby. Trace levels of contaminants may be acceptable in certain circumstances and such circumstances may be determined by the skilled person at the time. In general, levels of contaminant should be less than 1%, and preferably substantially less than 1%, for example less than 0.1%, possibly as low as 0.001%.

In the alternative, it is preferred that the compounds are non-toxic, by which is meant that the compounds should not exhibit any unacceptable levels of toxicity at the dosages at which they are applied. Preferably, they should exhibit no toxicity whatsoever.

Regardless of the foregoing, the class of compounds defined above is useful for neuroprotection under hypoxic or ischaemic conditions, and we have demonstrated this by tests on the hippocampus, as described below. The levels at which these compounds are active are substantially lower than those at which the prior art compounds are active.

The compounds of the present invention may be applied to the patient if it is suspected that they are in danger of an ischaemic event, especially a stroke or head injury. Such prophylactic application may be exceedingly useful. However, it has also been demonstrated that the compounds of the present invention have useful activity, even if applied after an ischaemic event, but it will be appreciated that it is preferred to administer the compounds as soon as possible, in order to avoid as much neuronal degeneration as possible. In some circumstances it may be desirable to administer repeated doses, especially where the patient remains in danger of an ischaemic event.

Suitable methods of administration are generally by injection, in order to achieve the desired result as soon as possible. Thus, intravenous injection is particularly preferred but, in some circumstances it may be preferable to administer the compound directly into the cerebrospinal fluid.

The dose of the compound of the present invention will vary depending upon many factors, including the age, body weight and general condition of the patient, as well as the mode, frequency and route of administration. However, a dose of from 0.01 to 50 mg/kg body weight is generally recommended, a dose of from 0.05 to 20 mg/kg body weight being more preferred. This may be administered in a single dose or in divided doses.

In the compounds of the present invention, it is generally preferred that the overall length of the compound is in the region of the length of Compound A, as shown hereafter. Compound A can be considered to be 18 units long, so that we prefer the compounds of the present invention should be no longer than 25 units long, and no shorter than 14 units long. This is a general preference, but it is generally noted that there is a rapid drop-off in activity with a length change of any significance, even one unit having a generally undesirable effect. Accordingly, it is more preferred that the compound should be from 17 to 22 units long. By "unit" is meant an atom in the longest chain, excluding hydrogen, and those non-chain atoms attached thereto. Thus, for example, in formula (Ia), the group —$NH_2$ is regarded as a unit, as are the groups $CR^2R^4$, CO, $CR^4R^6$, etc.

Q may represent a cyano group, an amidino group or a group of formula XYN—.

Where X or Y represents a lower alkyl group, this preferably has from 1 to 6 carbon atoms and may be a straight or branched chain group having from 1 to 6, preferably from 1 to 4, carbon atoms. Examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl ethyl, propyl, isopropyl, butyl and isobutyl groups, and most preferably the methyl group.

Where X or Y represents a simple hetero-atom containing group, this may be an acyclic or cyclic group. Examples of acyclic groups include the amidino group (to form, with the nitrogen atom to which X and Y are attached, a guanidino group), alkoxycarbonyl groups (to form an alkoxycarbonylamino group), the carbamoyl group or thiocarbamoyl group (to form the ureido group or the thioureido group). Examples of heterocyclic groups which may be represented by X and Y include those groups having from 5 to 10 ring atoms (in one or two rings), of which from 1 to 4 are nitrogen and/or oxygen and/or sulphur hetero-atoms, the remainder being carbon atoms. Where there are 4 hetero-atoms, we prefer that all 4 are nitrogen atoms. Where there are 3 hetero-atoms, we prefer that all 3, 2 or 1 are nitrogen atoms. Where there are 2 hetero-atoms, we prefer that 2 or 1 are nitrogen atoms. Examples of such groups include the pyrrolyl, tetrazolyl, indolyl, thiazolyl, furyl, pyranyl, chromenyl, imidazolyl, pyrazolyl, isothiazolyl, oxazolyl, isoxazolyl, pyridyl, pyrazinyl, pyrimidinyl, isoindolyl, quinolyl, isoquinolyl, carbazolyl, chromanyl, pyrrolidinyl, pyrrolinyl, imidazolidinyl, piperidyl, piperazinyl, indolinyl and morpholinyl groups.

Alternatively, X and Y, together with the nitrogen atom to which they are attached, may form a nitrogen-containing heterocyclic group. Examples of such heterocyclic groups include those groups having from 5 to 10 ring atoms (in one or two rings), of which from 1 to 4 are nitrogen and/or oxygen and/or sulphur hetero-atoms, the remainder being carbon atoms. Where there are 4 hetero-atoms, we prefer that all 4 are nitrogen atoms. Where there are 3 hetero-atoms, we prefer that all 3, 2 or 1 are nitrogen atoms. Where there are 2 hetero-atoms, we prefer that 2 or 1 are nitrogen atoms. Examples of such groups include the 1-pyrrolyl, 1- or 2-tetraaolyl, 1-indolyl, 3-thiazolyl, 1-imidazolyl, 1-pyrazolyl, 2-isothiazolyl, 3-oxazolyl, 2-isoxazolyl, 1-pyridyl, 1-pyrazinyl, 1-isoindolyl, 1-quinolyl, 2-isoquinolyl, 9-carbazolyl, 1-pyrrolidinyl, 1-pyrrolinyl 1-imidazolidinyl, piperidino, 1-piperazinyl, 1-indolinyl and morpholino groups.

Where Q represents an alkoxycarbonylamino group, the alkoxy part preferably has from 1 to 6 carbon atoms and may be a straight or branched chain group. Examples of such groups include the methoxycarbonylamino, ethoxycarbonylamino, propoxycarbonylamino, isopropoxycarbonylamino, butoxycarbonylamino, pentyloxycarbonylamino and hexyloxycarbonylamino groups, of which we prefer those groups having from 1 to 4 carbon atoms, and most prefer the ethoxycarbonylamino group.

Preferably at least one of X and Y represents a hydrogen atom. We particularly prefer that one or both of X and Y represents a hydrogen atom. Particularly preferred compounds are those compounds of formula (I) in which both X and Y represent hydrogen atoms or those in which one of X and Y represents a hydrogen atom and the other represents an amidino group or a carbamoyl group. The most preferred compounds are those compounds of formula (I), (Ia) and (Ib) in which both X and Y represent hydrogen atoms or those in which one of X and Y represents a hydrogen atom and the other represents an amidino group.

The length of the groups represented by $R^a$ and $R^b$, that is, in formula (Ia), the size of x in combination with y, is not particularly important, except that the preferred overall length of the compound is preferably observed. Whilst any particular alkylene or alkenylene group represented by $R^a$ may be as much as 6 carbon atoms long, it is preferred to restrict each alkylene chain to no more than 5, but preferably 3 or 4, carbon atoms, and an overall combination of trimethylene and tetramethylene groups is generally preferred. Examples of such alkylene and alkenylene groups include the methylene, ethylene, trimethylene, tetramethylene, pentamethylene, hexamethylene, vinylene, propenylene, but-1-enylene, but-2-enylene, pent-1-enylene, pent-2-enylene, pent-3-enylene, hex-1-enylene, hex-2-enylene, hex-3-enylene and hex-4-enylene groups. Thus, x is preferably 3 or 4, and y is preferably 3 or 4. Similarly, the alkylene or alkenylene group represented by $R^c$ is preferably a trimethylene or tetramethylene group. Where $R^b$ is a trimethylene group, $R^c$ is a tetramethylene group, and vice versa. Most preferably, $R^b$ is a trimethylene group and $R^c$ is a tetramethylene group.

The various groups $R^1$, $R^4$, $R^5$, $R^6$ and $R^7$ may be lower alkyl or aryl groups which may be unsubstituted or may be substituted by at least one of substituents α, defined above. The lower alkyl groups preferably have from 1 to 6 carbon atoms, and examples include the methyl, ethyl, propyl, isopropyl butyl, isobutyl, sec-butyl, t-butyl, pentyl, isopentyl, neopentyl, hexyl and isohexyl groups, of which the methyl and ethyl groups are preferred, the methyl group being most preferred. The aryl groups are carbocyclic aromatic groups which preferably have from 6 to 10 ring carbon atoms, and more preferably have 6 or 10 ring carbon atoms, for example the phenyl, 1-naphthyl and 2-naphthyl groups, of which the phenyl group is preferred. Alternatively, any of these groups may be substituted by one or more of substituents α.

Examples of substituents α include:

halogen atoms for example chlorine, fluorine or bromine atoms;

amino groups;

alkylamino groups, in which the alkyl part preferably has from 1 to 6 carbon atoms, for example the methylamino, ethylamino, propylamino, butylamino, t-butylamino, pentylamino and hexylamino groups;

dialkylamino groups, in which the alkyl part preferably has from 1 to 6 carbon atoms, for example the dimethylamino, diethylamino, methylethylamino, dipropylamino, dibutylamino, dipentylamino and dihexylamino groups;

cyano groups;

hydroxy groups;

alkyl groups (except when the substituted group is alkyl), for example as exemplified above in relation to $R^1$ etc.;

aryl groups, for example as exemplified above in relation to $R^1$ etc.;

carbamoyl groups;

alkylcarbamoyl groups, in which the alkyl part preferably has from 1 to 6 carbon atoms, for example the methylcarbamoyl, ethylcarbamoyl, propylcarbamoyl, butylcarbamoyl, t-butylcarbamoyl, pentylcarbamoyl and hexylcarbamoyl groups; and dialicylcarbamoyl groups, in which the alkyl part preferably has from 1 to 6 carbon atoms, for example the dimethylcarbamoyl, diethylcarbamoyl, methylethylcarbamoyl, dipropylcarbamoyl, dibutylcarbamoyl, dipentylcarbamoyl and dihexylcarbamoyl groups.

Examples of such substituted groups include: halogen-substituted methyl groups, preferably having three halogen atoms, such as the trichloromethyl and trifluoromethyl groups; halogen-substituted phenyl groups, such as the o-, m- and p-chlorophenyl, o-, m- and p-fluorophenyl, o-, m- and p-bromophenyl, 2,3-dichlorophenyl, 2,3-difluorophenyl, 3,4-dichlorophenyl, 3,4-difluorophenyl, 2,4,6-trichlorophenyl and 2,4,6-trifluorophenyl groups; amino-substituted alkyl groups, such as the aminomethyl, 2-aminoethyl, 3-aminopropyl and 4-aminobutyl groups; alkylamino-substituted alkyl groups (in which the alkyl part of the alkyl amino group preferably has from 1 to 4 carbon atoms), such as the methylaminomethyl, 2-methylaminoethyl, 3-methylaminopropyl, 4-methylaminobutyl, ethylaminomethyl, 2-ethylaminoethyl, 3-ethylaminopropyl, 4ethylaminobutyl, propylaminomethyl, 2-propylaminoethyl, 3-propylaminopropyl, 4-propylaminobutyl, butylaminomethyl, 2-butylaminoethyl, 3-butylaminopropyl and 4-butylaminobutyl groups; dialkylamino-substituted alkyl groups (in which each alkyl part of the dialkylamino group preferably has from 1 to 4 carbon atoms), such as the N,N-dimethylaminomethyl, 2-N,N-dimethylaminoethyl, 3-N,N-dimethylaminopropyl, 4-N,N-dimethylaminobutyl, N,N-diethylaminomethyl, 2-N,N-diethylaminoethyl, 3-N,N-diethylaminopropyl, 4-N,N-ethylaminobutyl, N,N-propylaminomethyl, 2-N,N-propylaminoethyl, 3-N,N-propylaminopropyl, 4-N,N-propylaminobutyl, N,N- butylaminomethyl, 2-N,N-butylaminoethyl, 3-N,N-butylaminopropyl and 4N,N-butylaminobutyl groups; aryl-(particularly phenyl or naphthyl) substituted alkyl groups, such as the benzyl, phenethyl, 3-phenylpropyl or 4-phenylbutyl groups; carbamoyl-substituted alkyl groups, such as the carbamoylmethyl, 2-carbamoylethyl, 3-carbamoylpropyl and 4-carbamoylbutyl groups; alkylcarbamoyl-substituted alkyl groups (in which the alkyl part of the alkylcarbamoyl group preferably has from 1 to 4 carbon atoms), such as the methylcarbamoylmethyl, 2-methylcarbamoylethyl, 3-methylcarbamoylpropyl, 4-methylcarbamoylbutyl, ethylcarbamoylmethyl, 2-ethylcarbamoylethyl, 3-ethylcarbamoylpropyl, 4-ethylcarbamoylbutyl, propylcarbamoylmethyl, 2-propylcarbamoylethyl, 3-propylcarbamoylpropyl, 4-propylcarbamoylbutyl, butylcarbamoylmethyl, 2-butylcarbamoylethyl, 3-butylcarbamoylpropyl and 4-butylcarbamoylbutyl groups; dialkylcarbamoyl-substituted alkyl groups (in which each alkyl part of the dialkylcarbamoyl group preferably has from 1 to 4 carbon atoms), such as the N,N-dimethylcarbamoylmethyl, 2-N,N-dimethylcarbamoylethyl, 3-N,N-dimethylcarbamoylpropyl, 4-N,N-dimethylcarbamoylbutyl, N,N-diethylcarbamoylmethyl, 2-N,N-diethylcarbamoylethyl, 3-N,N-diethylcarbamoylpropyl, 4-N,N-ethylcarbamoylbutyl, N,N-propylcarbamoylmethyl, 2-N,N-propylcarbamoylethyl, 3-N,N-propylcarbamoylpropyl, 4-N,N-propylcarbamoylbutyl, N,N-butylcarbamoylmethyl, 2-N,N-butylcarbamoylethyl, 3-N,N-butylcarbamoylpropyl and 4-N,N-butylcarbamoylbutyl groups; carboxy-substituted alkyl groups, such as the carboxymethyl, 2-carboxyethyl, 3-carboxypropyl and 4-carboxybutyl groups and esters thereof; and o-, m- and p-aminophenyl, methylaminophenyl, ethylaminophenyl, propylaminophenyl, butylaminophenyl, N,N-dimethylaminophenyl, N,N-diethylaminophenyl, N,N-dipropylaminophenyl, N,N-dibutylaminophenyl, biphenylyl, carbamoylphenyl, methylcarbamoylphenyl, ethylcarbamoylphenyl, propylcarbamoylphenyl, butylcarbamoylphenyl, N,N-dimethylcarbamoylphenyl, N,N-diethylcarbamoylphenyl, N,N-dipropylcarbamoylphenyl, N,N-dibutylcarbamoylphenyl and carboxyphenyl groups and esters of the carboxyphenyl groups.

Examples of ester groups include:

alkyl groups having from 1 to 20 carbon atoms, more preferably from 1 to 6 carbon atoms, such as those exemplified above and higher alkyl groups as are well known in the art, such as the heptyl, octyl, nonyl, decyl, dodecyl, tridecyl, pentadecyl, octadecyl, nonadecyl and icosyl groups, but most preferably the methyl, ethyl and t-butyl groups;

cycloalkyl groups having from 3 to 7 carbon atoms, for example the cyclopropyl, cyclobutyl, cyclopentyl, cyclohexyl and cycloheptyl groups;

aralkyl groups, in which the alkyl part has from 1 to 3 carbon atoms and the aryl part is a carbocyclic aromatic group having from 6 to 14 carbon atoms, which may be substituted or unsubstituted and, if substituted, has at least one of substituents α defined and exemplified above, although the unsubstituted groups are preferred; examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl, 2-(2-naphthyl)ethyl, benzhydryl (i.e. diphenylmethyl), triphenylmethyl, bis(o-nitrophenyl)-methyl, 9-anthrylmethyl, 2,4,6-trimethylbenzyl, 4-bromobenzyl, 2-nitrobenzyl, 4-nitrobenzyl, 3-nitrobenzyl, 4-methoxybenzyl and piperonyl groups;

alkenyl groups having from 2 to 6 carbon atoms, such as the vinyl, allyl, 2-methylallyl, 1-propenyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl groups, of which the vinyl, allyl, 2-methylallyl, 1-propenyl, isopropenyl and butenyl groups are preferred, the allyl and 2-methylallyl groups being most preferred.

halogenated alkyl groups having from 1 to 6, preferably from 1 to 4, carbon atoms, in which the alkyl part is as defined and exemplified in relation to the alkyl groups above, and the halogen atom is chlorine, fluorine, bromine or iodine, such as the 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl groups;

substituted silylalkyl groups, in which the alkyl part is as defined and exemplified above, and the silyl group has up to 3 substituents selected from alkyl groups having from 1 to 6 carbon atoms and phenyl groups which are unsubstituted or have at least one substituent selected from substituents a defined and exemplified above, for example a 2-trimethylsilylethyl group;

phenyl groups, in which the phenyl group is unsubstituted or substituted, preferably with at least one alkyl group having from 1 to 4 carbon atoms or acylamino group, for example the phenyl, tolyl and benzamidophenyl groups;

phenacyl groups, which may be unsubstituted or have at least one of substituents α defined and exemplified above, for example the phenacyl group itself or the p-bromophenacyl group;

cyclic and acyclic terpenyl groups, for example the geranyl, neryl, linalyl, phytyl, menthyl (especially m- and p-menthyl), thujyl, caryl, pinanyl, bornyl, notcaryl, norpinanyl, norbornyl, menthenyl, camphenyl and norbornenyl groups;

alkoxymethyl groups, in which the alkoxy part has from 1 to 6, preferably from 1 to 4, carbon atoms and may itself be substituted by a single unsubstituted alkoxy group, such as the methoxymethyl, ethoxymethyl, propoxymethyl, isopropoxymethyl, butoxymethyl and methoxyethoxymethyl groups;

aliphatic acyloxyalkyl groups, in which the acyl group is preferably an alkanoyl group and is more preferably an alkanoyl group having from 2 to 6 carbon atoms, and the alkyl part has from 1 to 6, and preferably from 1 to 4, carbon atoms such as the acetoxymethyl, propionyloxymethyl, butyryloxymethyl, isobutyryloxymethyl, pivaloyloxymethyl, 1-pivaloyloxyethyl, 1-acctoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy-2-methylpropyl, 1-propionyloxyethyl, 1-propionyloxypropyl, 2-acetoxypropyl and 1-butyryloxyethyl groups;

cycloalkyl-substituted aliphatic acyloxyalkyl groups, in which the acyl group is preferably an alkanoyl group and is more preferably an alkanoyl group having from 2 to 6 carbon atoms, the cycloalkyl substituent has from 3 to 7 carbon atoms, and the alkyl part has from 1 to 6, preferably from 1 to 4, carbon atoms, such as the (cyclohexylacetoxy)methyl, 1-(cyclohexylacetoxy)ethyl, 1-(cyclohexylacetoxy)propyl, 2-methyl-1-(cyclohexylacetoxy)propyl, (cyclopentylacetoxy)methyl, 1-(cyclopentylacetoxy)ethyl, 1-(cyclopentylacetoxy)propyl and 2-methyl-1-(cyclopentylacetoxy)propyl groups;

alkoxycarbonyloxyalkyl groups, especially 1-(alkoxycarbonyloxy)ethyl groups, in which the alkoxy part has from 1 to 10, preferably from 1 to 6, and more preferably from 1 to 4, carbon atoms, and the alkyl part has from 1 to 6, preferably from 1 to 4, carbon atoms, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-secbutoxycarbonyloxyethyl, 1-t-butoxycarbonyloxyethyl, 1-(1-ethylpropoxycarbonyloxy)ethyl and 1-(1,1-dipropylbuloxycarbonyloxy)ethyl groups, and other alkoxycarbonylalkyl groups, in which both the alkoxy and alkyl groups have from 1 to 6, preferably from 1 to 4, carbon atoms, such as the 2-methyl-1-(isopropoxycarbonyloxy) propyl, 2-(isopropoxycarbonyloxy)propyl, isopropoxycarbonyloxymethyl, t-butoxycarbonyloxymethyl, methoxycarbonyloxymethyl and ethoxycarbonyloxymethyl groups;

cycloalkylcarbonyloxyalkyl and cycloalkyloxycarbonyloxyalkyl groups, in which the cycloalkyl group has from 3 to 10, preferably from 3 to 7, carbon atoms, is mono- or poly-cyclic and is optionally substituted by at least one (and preferably only one) alkyl group having from 1 to 4 carbon atoms (e.g. selected from those alkyl groups exemplified above) and the alkyl part has from 1 to 6, more preferably from 1 to 4, carbon atoms (e.g. selected from those alkyl groups exemplified above) and is most preferably methyl, ethyl or propyl, for example the 1-methylcyclohexylcarbonyloxymethyl, 1-methylcyclohexyloxycarbonyloxymethyl, cyclopentyloxycarbonyloxymethyl, cyclopentylcarbonyloxymethyl, 1-cyclohexyloxycarbonyloxyethyl, 1-cyclohexylcarbonyloxyethyl, 1-cyclopentyloxycarbonyloxyethyl, 1-cyclopentylcarbonyloxyethyl, 1-cycloheptyloxycarbonyloxyethyl, 1-cycloheptylcarbonyloxyethyl, 1-methylcyclopentylcarbonyloxymethyl, 1-methylcyclopentyloxycarbonyloxymethyl, 2-methyl-1-(1-methylcyclohexylcarbonyloxy)propyl, 1-(1-methylcyclohexylcarbonyloxy)propyl, 2-(1-methylcyclohexylcarbonyloxy)propyl, 1-(cyclohexylcarbonyloxy)propyl, 2-(cyclohexylcarbonyloxy)propyl, 2-methyl-1-(1-methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentylcarbonyloxy)propyl, 1-(1-methylclopentylcarbonyloxy)ethyl, 1-(1-methylcyclopentylcarbonyloxy)propyl, adamantyloxycarbonyloxymethyl, adamantylcarbonyloxymethyl, 1-adamantyloxycarbonyloxyethyl and 1-adamantylcarbonyloxyethyl groups;

cycloalkylalkoxycarbonyloxyalkyl groups in which the alkoxy group has a single cycloalkyl substituent, the cycloalkyl substituent having from 3 to 10, preferably from 3 to 7, carbon atoms and mono- or poly-cyclic, for example the cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexylmethoxycarbonyloxy)ethyl groups;

terpenylcarbonyloxyalkyl and terpenyloxycarbonyloxyalkyl groups, in which the terpenyl group is as exemplified above, and is preferably a cyclic terpenyl group, for example the 1-(menthyloxycarbonyloxy)ethyl, 1-(menthylcarbonyloxy)ethyl, menthyloxycarbonyloxymethyl, menthylcarbonyloxymethyl, 1-(3-pinanyloxycarbonyloxy)ethyl, 1-(3-pinanylcarbonyloxy)ethyl, 3-pinanyloxycarbonyloxymethyl and 3-pinanylcarbonyloxymethyl groups;

5-alkyl or 5-phenyl [which may be substituted by at least one of substituents α, defined and exemplified above]

(2-oxo-1,3-dioxolen-4-yl)alkyl groups in which each alkyl group (which may be the same or different) has from 1 to 6, preferably from 1 to 4, carbon atoms, for example the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)-methyl, (5-t-butyl-2-oxo-1,3-dioxolen-4-yl) methyl and 1-(5-methyl-2-oxo-1,3-dioxolen-4-yl)ethyl groups; and other groups, especially groups which are easily removed in vivo such as the phthalidyl, indanyl and 2-oxo-4,5,6,7-tetrahydro-1,3-benzodioxolen-4-yl groups.

Of the above groups, we especially prefer those groups which can be removed easily in vivo, and most preferably the aliphatic acyloxyalkyl groups, alkoxycarbonyloxyalkyl groups, cycloalkylcarbonyloxyalkyl groups, phthalidyl groups and (5-substituted 2-oxo-1,3-dioxolen-4-yl)methyl groups.

However, we prefer that $R^1$, $R^4$, $R^5$, $R^6$ and $R^7$ are all hydrogen.

It is generally preferred that the group Z is not present, i.e. n is 0, but where it is present then it is preferably that it corresponds to the residue of an aromatic, and preferably hydrophobic aromatic, amino acid, more preferably an α-amino acid, such as histidine, phenylalanine, tyrosine, tryptophan or phenylglycine, of which phenylalanine or tyrosine are most preferred.

$R^c$ is a lower alkylene group optionally substituted by 1 or 2 alkyl, preferably methyl, groups. Such a lower alkylene group has 3 or 4 carbon atoms in a straight chain and is optionally substituted by 1 or 2 alkyl, preferably methyl, groups. Examples of such groups include the methylene, ethylene, methyl ethylene, 1-, 2- or 3-methyltrimethylene, trimethylene, propylene, tetramethylene, pentamethylene and hexamethylene groups, of which the trimethylene and tetramethylene groups are generally preferred.

Preferred compounds of the present invention are the following Compounds of formula A to D:

Compound of Formula A

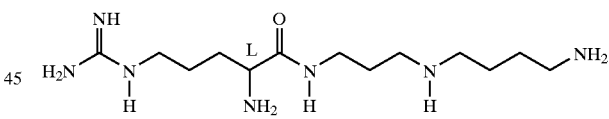

Compound of Formula B

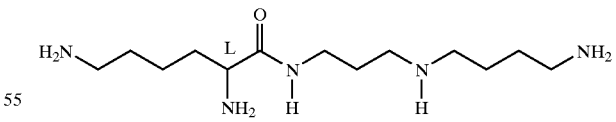

Compound of Formula C

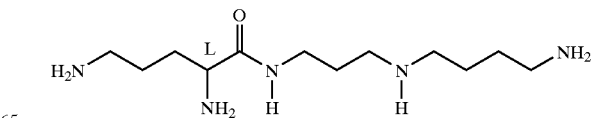

Compound of Formula D
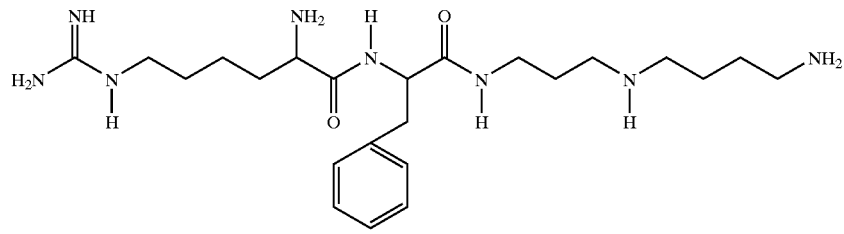
Compound of Formula E
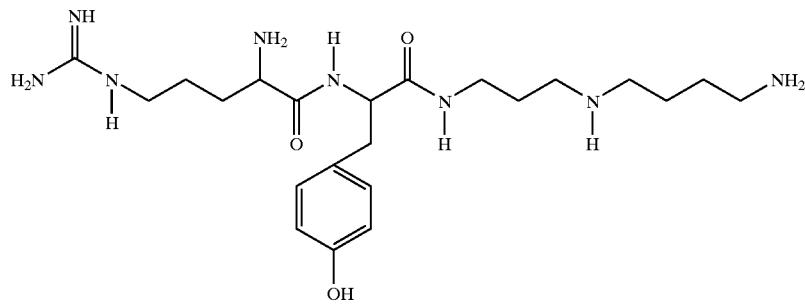
Compound of Formula F
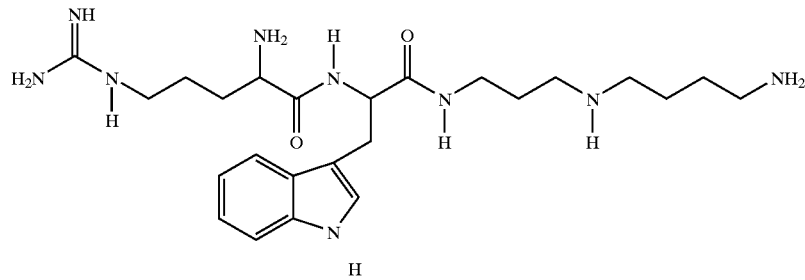
Compound of Formula G
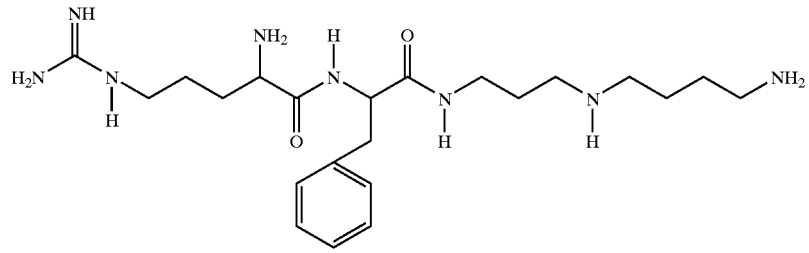

Compound of Formula H

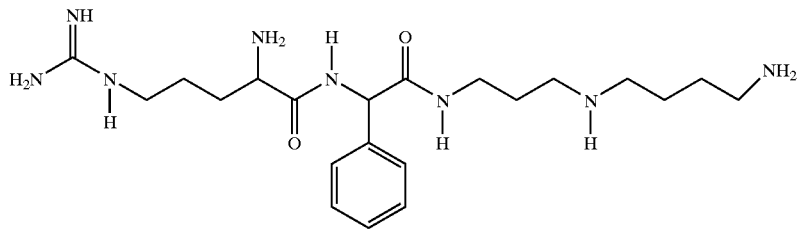

Compound of Formula I

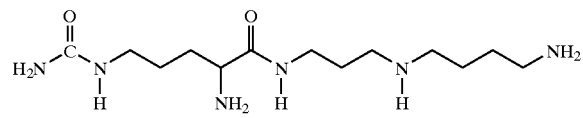

Of these, the Compounds of formula A, D, E, F, G, H and I are especially preferred, the Compounds of formula A and D being more preferred, and the Compound of formula A being most preferred.

The compounds of the present invention may be prepared by a variety of processes which, in themselves, are well-known in the art. Alternatively, they may be prepared by the following procedure:

Wang resin (0.03 mmol) is swollen in anhydrous tetrahydrofuran (1.0 ml) and carbonyl diimidazole (4 equivalents, 0.12 mmol) is added portion-wise. The resulting mixture is stirred at ambient temperature for 16 hours and then filtered, after which it is washed with tetrahydrofuran, ethanol and dichloromethane. The resin is then dried in vacuo.

The resin is re-swollen in anhydrous dichloromethane (1.0 ml) and 1,3-diaminopropane (10 equivalents, 0.3 mmol) is added portion-wise. The resulting mixture is stirred for 2 hours and then filtered, after which it is washed (dimethylformamide, methanol, dichloromethane) and then dried in vacuo.

The resin is again re-swollen in anhydrous dichloromethane (1.0 ml) and 2,6-lutidine (5 equivalents, 0.15 mmol) is added, followed by the careful addition of 2,4-dinitrobenzenesulfonyl chloride (4 equivalents, 0.12 mmol). The mixture is stirred under an inert atmosphere for 2 hours and then washed (dimethylformamide, methanol, dichloromethane) and dried in vacuo.

The resulting resin is then swollen in anhydrous tetrahydrofuran (1.0 ml) and triphenylphosphine (4 equivalents, 0.12 mmol), Dde-protected aminoalcohol (4 equivalents, 0.12 mmol) are added and dissolved with stirring. Diethylazodicarboxylate (4 equivalents, 0.12 mmol) is added dropwise and the mixture stirred for 12 hours and then filtered and washed (dimethylformamide, methanol, dichloromethane), after which it is dried in vacuo.

The resin is then swollen in dichloromethane (1.0 ml) and propylamine (5 equivalents, 0.15 mmol) is added and the mixture is stirred for 1 hour, after which it is filtered and washed (dimethylformamide, methanol, dichloromethane) and then dried in vacuo.

The resin is again swollen in dichloromethane (1.0 ml) and di-t-butyl dicarbonate (10 equivalents, 0.3 mmol) and N,N-dimethylaminopyridine (5 mol %, 0.0015 mmol) are added. The is then mixture stirred for 16 hours. The resin is then filtered and washed (dimethylformamide, methanol, dichloromethane) and then dried in vacuo.

The resin is then stirred in 2% hydrazine hydrate/dimethylformamide (1.0 ml) for 1 hour then washed (dimethylformamide, methanol, dichloromethane) and dried in vacuo.

Fmoc AA (4 equivalents, 0.12 mmol), TBTU (4 equivalents, 0.12 mmol), and diisopropylethylamine (8 equivalents, 0.48 mmol) are dissolved in anhydrous dimethylformamide (1.0 ml) and the mixture added to the resin. The whole is then stirred for 12 hours and then filtered and washed (dimethylformamide, methanol, dichloromethane) and dried in vacuo.

To the resin is added 20% piperidine/dimethylformamide (1.0 ml) and the mixture is stirred for 0.5 hour and then filtered and washed (dimethylformamide, methanol, dichloromethane), after which it is dried in vacuo.

Boc AA (4 equivalents, 0.12 mmol), TBTU (4 equivalents, 0.12 mmol), and diisopropylethylamine (8 equivalents, 0.48 mmol) are dissolved in dimethylformamide (1.0 ml) and the mixture is added to the resin. The whole is then stirred for 12 hours and then filtered and washed (dimethylformamide, methanol, dichloromethane), after which it is dried in vacuo.

50% TFA/45% dichloromethane/2.5% $H_2O$/2.5% triisopropylsilane (1.0 ml) is added to the resin and the mixture is stirred for 1 hour. The resin is filtered and washed with dichloromethane (1.0 ml) and the filtrate is concentrated in vacuo. The resulting viscous yellow oil is triturated with anhydrous diethyl ether (3×2 ml) to yield the required compound.

Preparation of the compounds of the invention, as well as neuroprotective activity is illustrated in the accompanying non-limiting examples. In these examples, the following abbreviations are used:

| | |
|---|---|
| Arg | arginine; |
| Boc | t-butoxycarbonyl; |
| DIC | di-isopropylcarbodiimide; |
| EDT | ethane-1,2-diol; |
| Fmoc | N-fluorenylmethoxycarbonyl; |
| HOBt | hydroxybenzotriazole; |
| Lys | lysine; |
| ODS | octadecylsilane |
| Orn | ornithine; |
| Phe | phenylalanine; |
| Pmc | $N^G$-2,2,5,7,8-pentamethylchroman-6-ylsulphonyl; |
| RP-HPLC | reverse phase high performance liquid chromatography; |
| TFA | trifluoroacetic acid; |

COMPOUND SYNTHESIS

EXAMPLE 1

N'-L-Arginylspermidine [Compound of Formula A]

0.152 g of $N^1$-Fluorenylmethoxycarbonyl-$N^4$-(4'-benzoyloxycarbonyl-(1'-phenoxy)ethanoamido resin)-$N^8$-t-butoxycarbonylspermidine was treated with 5 ml of a 20% v/v solution of piperdine in dimethylformamide. The resin was filtered, and then treated again with 5 ml of a 20% v/v solution of piperidine in dimethylformamide for a further 30 minutes. At the end of this time, the resin was filtered and washed, in that order, with 10 ml of dimethylformamide, 5 ml of methanol and finally twice, each time with 10 ml of methylene chloride. Fmoc-Arg(Pmc)OH (0.1027 g, 0.154 mmol) was dissolved in methylene chloride (9 ml), and then HOBt (0.021 g, 0.155 mmol) was added. After 10 minutes at room temperature, $N^4$-(4'-Benzoyloxycarbonyl (1'-phenoxy)ethanoamido resin)-$N^8$-t-butoxycarbonylspermidine (0.1032 g, 0.031 mmol) was added followed by DIC (24 ml, 0.155 mmol). The mixture was gently stirred at room temperature for 20 hours. Following a negative ninhydrin test the resin was filtered and washed with methylene chloride (1× ml), methanol (1×5 ml), methylene chloride (2×10 ml) then dried under vacuum. Fmoc removal was carried out as above. $N^1$-Arg(Pmc)-$N^4$-(4'-Benzoyloxycarbonyl-(1'-phenoxy)ethanoamido resin)-$N^8$-t-butoxycarbonylspermidine was deprotected/cleaved using TFA-phenol-water-triisopropylsilane-ethane-1,2-dithiol (EDT) (81.5:5:5:1:2.5 by volume; 2.5 ml) for 5 hours at room temperature. The resin was removed by filtration through a Pasteur pipette containing a tight plug of glass wool and washed with methylene chloride (4×4 ml). The solvent was removed in vacuo, the residue dissolved in $CH_3CN$ (1 ml) and poured into cold diethyl ether (25 ml) to give a white precipitate which was separated by centrifugation. The supernatant was decanted and the solid resuspended in diethyl ether (25 ml). The solid was again separated by centrifugation and the procedure repeated twice. The product was dissolved in water before freeze-drying. The product (19.2 mg) was analysed and purified by RP-HPLC (ODS, eluting isocratically with water/0.1% TFA).

EXAMPLE 2

Compounds B, C, $Z^1$, $Z^2$ and $Z^3$

These Compounds were prepared in an analogous manner using Fmoc-L-Lys(t-butoxycarbonyl), Fmoc-L-Orn(t-butoxycarbonyl), Fmoc-D-Arg(Pmc), Fmoc-D-Lys(t-butoxycarbonyl) and Fmoc-D-Orn(t-butoxycarbonyl), respectively.

Compound Analysis

N-L-Arginylspermidine (Compound of Formula A)

δH (300 MHz, $D_2O$): 3.86 (1H, t, J-6.6, Arg alpha-CH), 3.28–3.02 (4H, m), 2.95–2.78 (6H, m), 1.98–1.70 (4H, m), 1.68–1.40 (6H, m)

δC (75 MHz, $D_2O$): 173.1 (COOH), 159.6 (NH═C(NH-2)NH), 55.6 (CH), 49.6 (CH$_2$), 47.8 (CH$_2$), 42.9 (CH$_2$), 41.4 (CH$_2$), 39.1 (CH$_2$), 30.8 (CH$_2$), 28 1 (CH$_2$), 26.5 (CH$_2$), 26.3 (CH$_2$), 25.4 (CH$_2$)

M/Z: (ES+) 302.3 (M+H)$^+$, 416.3 (M+H+TFA)$^+$.

$N_1$-D-Arginylspermidine (Compound $Z^1$)

δH (360 MHz, $D_2O$): 3.78 (1H, t, J-6.5 Arg alpha-CH), 3.32–3.04 (4H, m), 3.03–2.83 (6H, m), 1.87–1.69 (4H, m), 1.68–1.55 (4H, m), 1.54–1.42 (2H, m)

δC (95 MHz, $D_2O$): 53.8 (CH), 47.7 (CH$_2$), 45.9 (CH$_2$), 41.1 (CH$_2$), 39.5 (CH$_2$), 37.2 (CH$_2$), 29.0 (CH$_2$), 26.2 (CH$_2$), 24.6 (CH$_2$), 24 4 (CH$_2$), 23 5 (CH$_2$)

M/Z: (ES+) 302.3 (M+H)$^+$, 416.3 (M+H+TFA)$^+$.

$N^1$-L-Lysinylspermidine [Compound of Formula B]

δH (360 MHz, $D_2O$): 3.84 (1H, t, J-6.6, Lys alpha-CH), 3.23 (2H, aft, J7.5), 3.09–2.80 (8H, m), 1.89–1.73 (4H, m), 1.72–1.49 (6H, m), 1.44–1.26 (2H, m);

M/Z: (ES+) 274.3 (M+H)$^+$, 410.3 (M+Na+TFA)$^+$.

$N^1$-D-Lysinylspermidine (Compound $Z^2$)

δH (360 MHz, $D_2O$): 3.84 (1H, t, J-6.5, Lys alpha-CH), 3.23 (2H, aft, J7.5), 3.09–2.84 (8H, m), 1.90–1.74 (4H, m), 1.73–1.50 (6H, m), 1.40–1.27 (2H, m)

M/Z: (ES+) 274.3 (M+H)$^+$, 388.4 (M+H+TFA)$^+$.

$N^1$-L-Ornithylspermidine [Compound of Formula C]

δH (360 MHz, $D_2O$): 3.94 (1H, t, J-6.6, Orn alpha-CH), 3.31 (2H, aft, J7.5), 3.18–2.89 (8H, m), 2.08–1.80 (4H, m), 1.78–1.52 (6H, m)

M/Z: (ES+) 260.3 (M+H)$^+$, 374.3 (M+H+TFA)$^+$.

$N^1$-D-Ornithylspermidine (Compound $Z^3$)

δH (360 MHz, $D_2O$): 3.88 (1H, t, J-6.6, Orn alpha-CH), 3.23 (2H, aft, J7.5), 3.10–2.80 (8H, m), 1.98–1.78 (4H, m), 1.75–1.50 (6H, m)

M/Z: (ES+) 260.3 (M+H)$^+$, 374.3 (M+H+TFA)$^+$.

HPLC Analysis

The compounds of the present invention were analysed by HPLC. The results showed that the compounds when made by the preferred process of the present invention were substantially free of original reactants.

EXAMPLE 3

Arginine-L-phenylalanine-spermidine: Compound of Formula G

Wang resin (0.03 mmol, 50 mg) was swollen in anhydrous tetrahydrofuran (1.0 ml) and carbonyl diimidazole (4 equivalents, 0.12 mmol, 19 mg) was added. The resulting mixture was then stirred at ambient temperature for 16 hours, after which it was filtered and washed with tetrahydrofuran, ethanol and dichloromethane. The resin was then dried in vacuo.

The resin was re-swollen in anhydrous dichloromethane (1.0 ml), and 1,4-diaminobutane (10 equivalents, 0.3 mmol 25 mg) were added. The resulting mixture was stirred for 2 hours and then filtered and washed (dimethylformamide, methanol, dichloromethane), after which it was dried in vacuo.

The resin was again re-swollen in anhydrous dichloromethane (1.0 ml), and 2,6-lutidine (5 equivalents, 0.15 mmol, 16 mg) were added, followed by the careful addition of 2,4-dinitrobenzenesulfonyl chloride (4 equivalents, 0.12 mmol, 32 mg). The mixture was stirred under an inert atmosphere for 2 hours and then washed (dimethylformamide, methanol, dichloromethane) and dried in vacuo.

The resulting resin was then swollen in anhydrous tetrahydrofuran (1.0 ml) and triphenylphosphine (4 equivalents, 0.12 mmol, 32 mg). Dde-protected aminoalcohol (4 equivalents, 0.12 mmol, 29 mg) were added and dissolved with stirring. Diethyl azodicarboxylate (4 equivalents, 0.12 mmol, 21 mg) was added dropwise and the mixture was stirred for 12 hours and then filtered and washed (dimethylformamide, methanol, dichloromethane). It was then dried in vacuo.

The resin was then swollen in dichloromethane (1.0 ml), and propylamine (5 equivalents, 0.15 mmol, 13 mg) was added. The mixture was then stirred for 1 hour after which it was filtered and washed (dimethylformamide, methanol, dichloromethane) and then dried in vacuo.

The resin was again swollen in dichloromethane (1.0 ml), and dibutyl dicarbonate (10 equivalents, 0.3 mmol, 33 mg) and N,N-dimethylaminopyridine (5 mol %, 0.0015 mmol, 0.2 mg) were added, and the mixture was stirred for 16 hours. The resin was then filtered and washed (dimethylformamide, methanol, dichloromethane), and then dried in vacuo.

The resin was then stirred in 2% hydrazine hydrate/dimethylformamide (1.0 ml) for 1 hour and then washed (dimethylformamide, methanol, dichloromethane), after which it was dried in vacuo.

Fmoc-Phe-OH (4 equivalents, 0.12 mmol, 46 mg), TBTU (4 equivalents, 0.12 mmol, 39 mg) and diisopropylethylamine (8% 0.48 mmol, 62 mg) were dissolved in anhydrous dimethylformamide (1.0 ml), and the mixture was added to the resin. The whole was then stirred for 12 hours, and then filtered and washed (dimethylformamide, methanol, dichloromethane) and dried in vacuo.

To the resin was added 20% piperidine/dimethylformamide (1.0 ml) and the mixture was stirred for 0.5 hour. It was then filtered and washed (dimethylformamide, MEOH, dichloromethane) and then dried in vacuo.

Boc-Arg(Phe-OH (4 equivalents, 0.12 mmol, 63 mg), TBTU (4 equivalents, 0.12 mmol, 39 mg), and diisopropylethylamine (8 equivalents, 0.48 mmol, 62 mg) were dissolved in dimethylformamide (1.0 ml) and the mixture was added to the resin. The whole was then stirred for 12 hours and then filtered and washed (dimethylformamide, methanol, dichloromethane). It was then dried in vacuo.

50% TFA/45% dichloromethane/2.5% $H_2O$/2.5% triisopropylsilane (1.0 ml) was added to the resin and the mixture was stirred for 1 hour. The resin was filtered and washed with dichloromethane (1.0 ml) and the filtrate was concentrated in vacuo. The resulting viscous yellow oil was triturated with anhydrous diethyl ether (3×2 ml) to yield the title compound as its tetrakis TFA salt (1 9 mg, 700/o):

Analysis

LCMS

90% (ELS detection). M/z 449 ($ES^+$).

NMR:

$^1H$ NMR was found to be in accordance with the above structure

Dde protected aminoalcohol:

Dde=N-1-(4,4-dimethyl-2,6-dioxocyclohex-1-ylidene) ethyl

Preparation of Dde Protected Aminoalcohol

To a solution of 3-amino-1-propanol (1.5 g, 20 mmol) in ethanol was added 2-acetyl dimedone (1.1 equivalents, 22 mmol 4.0 g) and the mixture was heated to 50° C. for 1 hour. The resulting solution was concentrated in vacuo to yield a red crystalline solid that was triturated with hexane to afford an off-white solid (4.74 g, 95%)

EXAMPLE 4

Compound of Formula D

A PTFE 2 ml syringe was filled with $N^1$-Fluorenylmethoxycarbonyl-$N^4$-(4'-benzoyloxycarbonyl (1'-phenoxy)ethanoamido resin)-$N^8$-Bocspermidine (≈31 mg, 0.263 mmol/g) and treated 3 times with 20% piperidine in dimethylformamide (2 ml) for 30 minutes, followed by washing with dimethylformamide (2×2 ml) and $CH_2Cl_2$ (4×2 ml).

The resulting primary amine was coupled to Fmoc-Phe) using 5 equivalents (0.041 mmol) of the Fmoc-carbamoyl acid and DIC/HOBt activation in $CH_2Cl_2$/dimethylformamide (1 ml/1 drop). After 4 hours with occasional stirring, ninhydrin tests indicated that the couplings was complete. After treatment with 20% piperidine in dimethylformamide (2 ml, 2×30 mn) and washing with dimethylformamide (2×2 ml) and $CH_2Cl_2$ (4×2 ml) Di(Boc)-protected guanidino carboxylic acid was coupled to the sample. Coupling was achieved using 3 equivalents (0.025 mmol) of the carboxylic acid with DIC/HOBt activation in $CH_2Cl_2$/dimethylformamide (1 ml/1 drop). After 5 hours with occasional stirring, ninhydrin tests showed that the coupling was complete.

After washing with dimethylformamide (2×2 ml) and $CH_2Cl_2$ (4×2 ml), the compound was deprotected-cleaved from the solid support, the resin being pre-swollen in $CH_2Cl_2$ (1 ml) prior to treatment with TFA-$H_2O$ (95:5, 0.4 ml) for 1.5 hours.

The resin sample was washed with TFA-$CH_2Cl_2$ (1:1, 2 ml) and then the wash filtered into a vial. The solvent was reduced in vacuo and the residue was dissolved in water, frozen and lyophilised. The compound was analysed by ES MS and gave the desired molecular ion as the major peak.

M/Z: ($ES^+$) 448.4

EXAMPLE 5

Protocol for Studying Hypoxic Neuronal Damage

Hypoxic neuronal damage was studied using organotypic hippocampal slice cultures [Pringle A. K. et al. (1996 Stroke 27 2124–2130)].

Cultures were prepared according to the method of Stoppini et al (1991 J. Neurosci. Meth. 37 173–182) from 8–10 day old Wistar rat pups (Bioresources Unit, University of Southampton). Cultures were maintained in vitro for 14 days (37° C., 5% $CO_2$) during which the medium (50% minimum essential medium (MEM), 25% Hank's balanced salt solution (HBSS), 25% heat-inactivated horse serum, supplemented with 1 mM glutamine, 5 mg/ml glucose and 1.5% fungizone) was changed every 3 days. Hypoxia was induced by replacing culture medium with serum-free (SF) medium (75% MEM, 25% HBSS, 1 mM glutamine, 5 mg/ml glucose, 1.5% fungizone) saturated with 95% $N_2$/5% $CO_2$ (and thus oxygen-free), and placing cultures in an air-tight chamber in which the atmosphere was also saturated with $N_2$/$CO_2$. After 180 minutes hypoxia, cultures were replated in normoxic SF medium and replaced in the incubator for 24 hours. Compounds were added to cultures either pre-, during and post-hypoxia (herein abbreviated to "pdp") or just in the post-hypoxic recovery period ("post") [Johnson, T. D. (1996 Trends Pharmacol. Sci. 22–27)]. Cell damage was evaluated using the fluorescent exclusion dye propidium iodide (PI, 5 μg/ml) which is normally excluded from healthy cells, but enters cells with damaged plasma membranes and becomes highly fluorescent when bound to DNA. Neuronal cell damage was quantified using the "NIH Image 1.55" software (written by Wayne Rasband at the U.S. National Institutes for Health and available from the internet by anonymous ftp from zippy.nimh.nih.gov). Briefly, the area of the CA1, CA3 and dentate gyrus (DG) cell layers was measured from a transmission image. 24 hours after the commencement of hypoxia, a fluorescence image was captured using a standard Leica inverted fluorescence microscope fitted with a rhodamine filter set. The area of PI fluorescence above background in the neuronal cell layers was determined using the density slice function of Image. Cellular damage is expressed as the percentage area of the cell body layers in which PI fluorescence was detectable. After imaging, cultures were fixed overnight in 4% paraformaldehyde and stained with thionin.

Data are expressed as the mean±sem. Data from the non-drug groups was pooled before analysis. Statistical significance was determined using one-way analysis of variance (ANOVA) followed by post-hoc non-paired Student's t-tests. As only cells within the CA1 region were susceptible to hypoxia-induced damage, all of the pharmacological data was calculated for this region alone.

Protocol for Studying NMDA Receptor-mediated Neurotoxicity

Organotypic hippocampal slice cultures were prepared and maintained as described above. NMDA was prepared as a 50 mM stock solution in distilled water, and diluted as required in SF medium. Neurotoxicity was induced by placing cultures in SF medium containing either 10 μM or 30 ∞M NMDA for 180 minutes. After this time, cultures were replated in SF-medium and maintained for 24 hours in the incubator. Either 300 μM L-ArgSp or vehicle (SF medium) was added to the culture medium pre-, during and post-NMDA exposure. Throughout the duration of the experiment, 5 μg/ml PI was included in the medium. After 24 hours, neuronal damage was determined by PI fluorescence imaging and quantified as described previously.

Blood Flow Studies

Adult male Wistar rats (250–300 g) were initially anesthetized with 4% halothane and subsequently anaesthesia was maintained with 1.5% halothane mixed in 7% $N_2O$ in $O_2$. The femoral artery was cannulated for continuous blood pressure recording. The femoral vein was also cannulated to allow injection of the compound. Animals were allowed 15–30 minutes to stabilise and were then injected with 0.25–0.3 ml of a 1 mg/ml solution of L-ArgSp. Following injection of the compound, rats were continuously monitored for 60 minutes. After this time, anaesthesia was terminated and rats allowed to waken. In these studies, measurement was taken of the mean arterial blood pressure (MABP) induced following an intravenous injection of 1 mg/kg L-ArgSp into the femoral vein of anaesthetised male Wistar rats. MABP was calculated immediately prior to injection of L-ArgSp (pre-injection) and 30 seconds and 10 minutes post-injection. Data are presented as mean Used of four observations.

Global Forebrain Ischaemia

Animals were anaesthetised as described above, and a thermistor inserted into the left temporal muscle for recording of body temperature. A dorsal midline skin incision was made in the neck and using microsurgery, the vertebral arteries were identified and occluded using a monopolar electrode at the level of C 1. The incision was closed, animals allowed to recover from anaesthesia and returned to their cages for 24 hours. After this time, animals were re-anaesthetised and the common carotid arteries (CCAs) exposed. Animals were divided into two groups. Group 1 received 0.25–0.3 ml of a 1 mg/ml solution of L-ArgSp (final dose 1 mg/kg) while group 2 received 0.25–0.3 ml of sterile distilled water. Samples were prepared independently and randomised prior to injection. Animals were injected 15 minutes prior to occlusion of the CCAs with microvascular clips for 15 minutes. After this time, the skin was closed, and animals allowed to recover. After 24 hours animals were terminally anaesthetised and transcardially perfused with 1% paraformaldehyde and the brains removed and processed for histology. A blinded observer determined the number of live and dead neurones in the CA1, CA3 fields of the pyramidal cell layer, and the dentate gyrus granule cell layer from haematoxylin and eosin stained coronal sections.

Results (i) Control Procedures

After 14 days in vitro, organotypic hippocampal slice cultures retained much of the structure and morphology of the in vivo hippocampus. Specifically, clearly identifiable pyramidal (CA1 and CA3/4) and dentate gyrus granule cell layers were visible in thionin stained sections. Neurons appeared healthy, with large, lightly-stained nuclei surrounded by intensely-staining cytoplasm (FIG. 1).

24 hours after 3 hours hypoxia, PI fluorescence was detectable in the CA1 region of the pyramidal cell layer (35.6±1.43% damage, n=108), with little (but not statistically significant) PI labelling in either the CA3 pyramidal cells (7.1±1.3%) or dentate granule cells (3.9±2.9%). Little PI fluorescence was observed in untreated controls maintained in serum-free medium for 24 hours. After thionin-staining, control cultures were indistinguishable from untreated slices, with large, healthy appearing neurones. In contrast, in cultures exposed to 180 minutes hypoxia the CA3 pyramidal cells and dentate granule cells appeared normal, but cells in CA1 had small, darkly-staining, pyknotic nuclei with little visible cytoplasm indicating neuronal death—as shown in FIG. 1. FIG. 1 shows PI fluorescence images of untreated control culture (A) or culture 24 hours after a 3 hours hypoxia (B). No PI fluorescence is detectable in the untreated culture, but intense staining is present in the CA1 pyramidal cell layer of the hypoxia-treated culture. (C+D) Corresponding thionin-stained sections of CA1 region of the cultures shown in A+B. (C) Neurones contain lightly-stained nucleus surrounded by darkly-staining cytoplasm (white arrow). (D) In contrast, neurones in the hypoxia-treated cultures appear as small, darkly-staining pyknotic nuclei (black arrow). On this Figure, the scale bars are: A, B: 1 mm; C, D: 100 µm.

(ii) Effects of L-Arginylspermidine (Compound A)

After incubation with 300 µM L-ArgSp for 24 hours, no increase in PI fluorescence above baseline was observed. Addition of 300 µM L-ArgSp for 30 minutes prior to hypoxia, during the hypoxic episode and the 24 hour recovery period was completely neuroprotective. PI fluorescence was detectable in 0.2±0.02% of CA1 (n=12, p<0.001 vs hypoxia controls). In thionin stained slices, the neurons were indistinguishable from those of untreated or control cultures.

When the addition of the L-ArgSp was delayed until immediately post-hypoxia, a significant neuroprotective effect was still observed. This was concentration dependent (0.3–300 µM), with the $EC_{50}$ lying between 3 and 30 µM. The damage observed in the CA1 subfield in these cultures was reduced (see FIG. 1, Table 1—shown below) demonstrating that delaying the addition of the compound did not significantly reduce the neuroprotective efficacy.

TABLE 1

| Compound | n | % Damage CA1 | % Protection |
|---|---|---|---|
| Control Hypoxia | 108 | 35.6 ± 1.43 | |
| (A) L-ArgSp (300 µM) pre | 12 | 0.2 ± 0.02*** | 99.4 |
| (A) L-ArgSp (300 µM) | 16 | 9.9 ± 3.5*** | 72.2 |
| ($Z^1$) D-ArgSp (300 µM) | 8 | 32.6 ± 4.1 | 8.4 |
| (B) L-LysSp (300 µM) | 16 | 27.0 ± 3.7* | 24.2 |
| ($Z^2$) D-LysSp (300 µM) | 14 | 36.3 ± 3.5 | 0 |
| (C) L-OrnSp (300 µM) | 12 | 30.6 ± 3.8 | 14.0 |
| ($Z^3$) D-OrnSp (300 µM) | 11 | 36.71 ± 3.2 | 0 |
| L-Arg (300 µM) | 11 | 38.5 ± 4.0 | 0 |
| D-Arg (300 µM) | 10 | 32.7 ± 7.0 | 8.1 |
| Spermidine (300 µM) | 12 | 34.2 ± 5.4 | 3.9 |

Table 1 represents the quantification of the percentage area of the CA1 pyramidal cell layer in which PI fluorescence was detectable 24 hours after 3 hours of hypoxia (% Damage CA1). Data from all of the cultures exposed to hypoxia alone were pooled (control hypoxia). The percentage neuroprotection was calculated as the (((% damage control hypoxia-% damage drug treated)/% damage control hypoxia) 100). Data are expressed as the mean±sem, n=number of cultures, *p<0.05, <0.01, *p<0.001 vs hypoxia control.

To determine whether both the spermidine and arginine components of the L-ArgSp were essential for the generation of the neuroprotective effect, we also assessed the effects of post-hypoxic addition of 300 µM spermidine and 300 µM L-arginine.

Neither spermidine nor L-arginine individually produced a reduction in damage (see Table 1). These data indicate that it is necessary to have a compound having the structure as defined above—such as a compound prepared by conjugating L-arginine with spermidine—for the neuroprotective efficacy. This result is in contrast to the findings of WO 91/00853 wherein it is claimed that spermidine directly blocks calcium conductances. With our present work, we have shown that purified spermidine has no neuroprotective effects in our assay. At this stage, we believe that the difference is attributable to the fact that in WO 91/00853 no purification was attempted with the spermidine and so one can only postulate that the spermidine used was impure.

iii) Effect of Changing the Carbamoyl Acid Side Chain

When the arginine residue was replaced with the related carbamoyl acids lysine or ornithine, the neuroprotective efficacy of the resulting compounds was less than L-ArgSp. Nevertheless, neuroprotective efficacy was still observed. Addition of 300 µM L-lysinylspermidine (L-LysSp) immediately post hypoxia produced a small but significant reduction in PI fluorescence in the CA1 region (see Table 1). Post-hypoxic addition of 300 µM L-ornithylspermidine (L-OrnSp) produced less of a significant reduction in damage.

iv) Stereospecificity of the Neuroprotective Effect

Substitution of the L-carbamoyl acids with their respective D-enantiomers produced a profound reduction of the neuroprotective efficacy of the compounds relative to the L-enantiomers, as addition of 300 μM D-ArgSp, D-LysSp or D-OrnSp post-hypoxia did not result in any observable reduction of PI fluorescence (see Table 1 supra). In addition, cells of the CA1 subfield appeared with shrunken, darkly-staining, pyknotic nuclei indicating neuronal death. These results clearly demonstrate that we have found that L optical activity is important for neuroprotective efficacy. Hence, highly preferred compounds of the present invention have L optical activity. Furthermore, and in direct contrast to the teachings of WO 91/00853, we found that substituting lysine for arginine (compound A and B) reduces the neuroprotective action but does not reverse it.

v) Histogram

FIG. 2 presents an histogram demonstrating the concentration-dependent neuroprotective effect of L-ArgSp (0.3–300 μM) when added immediately post-hypoxia. Neuronal damage is expressed as the percentage of the area of CA1 in which PI fluorescence was measured 24 hours following three hours of hypoxia (% Damage CAT). (*p<0.001, p<0.01, *p<0.5 vs control hypoxia (control).

n=108 control. n=140.3 μM, n=7 3 μM, n=14 30 μM, n=16 300 μM).

vi) L-ArgSp Does Not Prevent NMDA-mediated Neuronal Damage 24 hours after 180 minutes exposure to 10 μM NMDA, PI fluorescence was detectable in the CA1 subfield of the pyramidal cell layer, but not other areas of the cultures. Increasing the concentration of NMDA to 30 μM produced a more severe insult, with significant neuronal damage occurring in both the CA1 and CA3 regions of the pyramidal cell layer, but with sparing of the granule cells of the dentate gyrus. Addition of 300 μM L-ArgSp to the medium throughout the experiment did not reduce the damage produced by either 10 μM or 30 μM NMDA. FIG. 3 shows a histogram demonstrating the lack of neuroprotective efficacy of L-ArgSp against NMDA-mediated neurotoxicity when added post-NMDA. Neuronal damage is expressed as the percentage area of either CA1 (solid bars) or CA3 (hatched bars) in which PI fluorescence was measured 24 hours after 180 minutes exposure to NMDA. (mean±sem, n=8 for each group).

vii) Blood Flow Studies

The results of these studies are presented in the Table 2 presented below.

TABLE 2

| Time | MABP (mmHg) | % Charge |
| --- | --- | --- |
| pre-injection | 79.9 ± 3.9 | |
| 30 secs | 72.2 ± 5.1 | −9.6 |
| 10 minutes | 79.2 ± 6.5 | −0.9 |

The blood pressure recordings were made 60 minutes after injection, immediately before the rat was wakened, were identical to those 10 minutes post-drug administration. The small reduction in MABP produced by L-ArgSp was not statistically significant. No effect on either body temperature or heart rate occurred in these animals following administration of L-ArgSp. Following wakening, no ill effects of the compound on the animals was observed. A further five rats have been allowed to recover for three days following administration of 1 mg/kg L-ArgSp and no long-term behavioural deficits have been observed in these animals.

viii) L-ArgSp Reduces Neuronal Damage Following Global Forebrain Ischaemia in vivo Fifteen minutes global forebrain ischaemia is a particularly severe insult, producing neuronal damage throughout the hippocampal formation. When assessed 24 hours after ischaemia, animals which received vehicle alone showed a neuronal loss in CA1, CA3 and the dentate gyrus with severity being regionally dependent (CA1>CA3>DG). In animals treated with 1 mg/kg L-ArgSp 15 minutes prior to induction of ischaemia, the neuronal loss was significantly attenuated, particularly in the extremely vulnerable CA1 region. This data is described in FIG. 4 which presents a histogram demonstrating the percentage of live neurones (as determined histologically) (% Live Neurones) in CA1, CA3 and the dentate gyrus (DG) of both vehicle-treated (solid bars) and L-ArgSp-treated animals (hatched bars). (**P<0.01, *P<0.05 vs vehicle-treated controls; data represents mean±sem, n=5 control, n=7 L-ArgSp).

Example Discussion

Using solid phase chemistry techniques we have synthesised, among others, arginylspermidine. We have shown that this compound, in particular the L-enantiomer, possesses significant neuroprotective efficacy, even if the addition of the compound was delayed until after the termination of the hypoxic episode.

The data demonstrate that the compounds of the present invention must comprise the above-mentioned first component linked to the above-mentioned second component via an amide bond—such as conjugated spermidine and L-Arg—to have neuroprotective efficacy. In this regard, no efficacy was detected using spermidine and L-Arg on their own. One conclusion that could, therefore, be drawn is that the action of the compound of the present invention, in particular L-ArgSp, is mediated through a receptor site which requires the presence of both the first and the second components in the same molecule.

Substitution of L-arginine with L-lysine (L-LysSp) or ornithine (L-OrnSp) still yields active compounds. However, the activities of these compounds are not as great as that for L-ArgSp. This suggests that the guanidinium functionality is desirable for optimal activity but that other positively charged groups can take its place relatively successfully.

It is currently believed therefore that a highly preferred feature for activity is the relative spatial positioning of the terminal positive charge on the guanidinium or ammonium ion and the alpha-carbamoyl group. This is suggested by the relative length of the side chains and their reduction in overall length in going from Arg to Lys to Orn and suggests that the compounds are capable of exhibiting a bi-functional binding ability.

Also, in a highly preferred embodiment of the present invention, it appears that the binding site appears to be stereospecific, requiring the carbamoyl acid to be in the L-configuration for optimal activity. Both D-ArgSp and D-LysSp were inactive relative to their corresponding L-enantiomers.

The blood flow data show that the compounds of the present invention, in particular the Compound of formula A, have a less adverse effect on blood flow than FTX.

EXAMPLE 6

The procedures of Example 5 were repeated, but using different doses of a fresh batch of Compound A (pdp). The results are shown in the following Table 3.

TABLE 3

| Compound | n | % Damage CA1 | % Protection |
| --- | --- | --- | --- |
| None (Control Hypoxia) | 50 | 23.9 ± 2.7 | — |
| 0.3 μM Compound A pdp | 8 | 20.2 ± 8.4 | 15.5 |
| 1 μM Compound A pdp | 8 | 20.1 ± 8.2 | 15.9 |
| 3 μM Compound A pdp | 15 | 6.5 ± 3.0** | 72.8 |
| 10 μM Compound A pdp | 7 | 8.8 ± 3.9* | 63.2 |
| 30 μM Compound A pdp | 8 | 7.3 ± 4.2* | 65.9 |
| 300 μM Compound A pdp | 16 | 8.0 ± 3.0** | 66.5 |

*p < 0.05,
**p < 0.01

EXAMPLE 7

The procedures of Example 5 were repeated, but using various compounds derived from Compound A by substitution at the α-amino group. The results are shown in the following Table 4.

TABLE 4

| Compound | n | % Damage CA1 | % Protection |
| --- | --- | --- | --- |
| None (Hypoxia) | 25 | 27.5 ± 3.2 | — |
| 300 μM NαCBZ-Compound A pre | 11 | 9.3 ± 4.3** | 66.2 |
| 300 μM NαCBZ-Compound A post | 12 | 12.4 ± 4.3** | 54.9 |
| None (Hypoxia) | 57 | 21.3 ± 2.4 | — |
| 0.3 μM NαCBZ-Compound A post | 8 | 16.6 ± 7.2 | 22.1 |
| 3 μM NαCBZ-Compound A post | 15 | 16.7 ± 4.0 | 21.6 |
| 30 μM NαCBZ-Compound A post | 14 | 14.8 ± 4.5 | 30.5 |
| 300 μM NαCBZ-Compound A post | 14 | 9.0 ± 2.7* | 57.7 |
| None (Hypoxia) | 33 | 20.3 ± 2.4 | — |
| 300 μM Nαacetyl-Compound A pre | 15 | 10.4 ± 4.0* | 48 |
| 300 μM Nαacetyl-Compound A post | 20 | 16.3 ± 3.1 | 18.5 |
| None (Hypoxia) | 49 | 26.8 ± 4.1 | — |
| 300 μM Nαbenzyl-Compound A post | 8 | 6.4 ± 4.9** | 76.1 |

*p < 0.05
**p < 0.01
CBZ = benzyloxycarbonyl

EXAMPLE 8

The procedures of Example 5 were repeated, but using a compound (PyrAla3,4) in which the arginine of Compound A is replaced by pyridylalanine. The results are shown in the following Table 5.

TABLE 5

| Compound | n | % Damage CA1 | % Protection |
| --- | --- | --- | --- |
| None (Hypoxia) | 40 | 28.4 ± 2.3 | — |
| 300 μM PyrAla3,4 post | 7 | 29.9 ± 3.7 | −5.3 |

It can be seen that this compound has a negative protective effect.

EXAMPLE 9

The procedures of Example 5 were repeated, but using either Compound I (in which the arginine of Compound A is replaced by citrulline) or a compound in which the arginine of Compound A is replaced by glutamine (Gln3,4). The results are shown in the following Table 6.

TABLE 6

| Compound | n | % Damage CA1 | % Protection |
| --- | --- | --- | --- |
| None (Hypoxia) | 16 | 23.2 ± 4.9 | — |
| 300 μM Compound I post | 7 | 10.9 ± 5.7* | 53 |
| 300 μM Gln3,4 post | 8 | 19.8 ± 6.5 | 14.7 |

*p < 0.05,

It can be seen that, whereas Compound I exerts a significant protective effect, Gln3,4 has no such effect.

EXAMPLE 10

The procedures of Example 5 were repeated, but using either Compound A or a compound corresponding to Compound A but in which $R^c$ is a tetramethylene group, i.e. the total number of carbon atoms in $R^b$ and $R^c$ is 8 (Arg4,4). The results are shown in the following Table 7.

TABLE 7

| Compound | n | % Damage CA1 | % Protection |
| --- | --- | --- | --- |
| None (Hypoxia) | 15 | 27.7 ± 3.1 | — |
| 300 μM Compound A post | 8 | 12.1 ± 3.5** | 56.3 |
| 300 μM Arg4,4 post | 7 | 26.7 ± 2.1 | 3.6 |

**p < 0.01

It can be seen that, whereas Compound A exerts a significant protective effect, Arg4,4 has no such effect.

Conclusion of Examples

In summation, a number of spermidine (polyamine) based compounds were synthesised using a novel solid phase approach and evaluated for their protective effects against hypoxia-induced neuronal damage in hippocampal slice cultures. The neuroprotective effects of 300 μM L-arginylspermidine were dramatic with complete protection being observed when added pre-hypoxia. When added post hypoxia, protection was observed in a concentration-dependent manner with substantial protection (>70%) at 300 μM with an EC 50 of from 3–30 μM. L-lysinylspermidine and L-ornithylspermidine were also protective, although to a lesser extent than the arginylspermidine. Significantly, the D-enantiomers of all three compounds were substantially less active (if at all) in providing neuroprotective activity than the L-enantiomers.

The amalgamation of solid phase/combinatorial chemistry and in vitro models of neuronal damage (e.g. ischaemia related damage) provide an excellent means to synthesise and investigate large numbers of potentially neuroprotective compounds. This approach presents the possibility of the generation of compounds which may profoundly influence the treatment of severe neurological damage such as that occurring after stroke.

What is claimed is:

1. A substantially pure compound having less than 1% contaminants and having the formula (I)

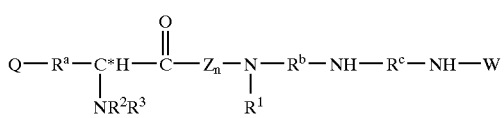
(I)

wherein:
- Q represents an amidino group, a cyano group or a group of formula XYN—, where
  - X and Y are the same or different, and each may represent a hydrogen atom, a lower alkyl group, or hetero-atom containing group or, together with the nitrogen atom to which they are attached, form a nitrogen-containing heterocyclic group;
- $R^a$ represents a straight or branched chain alkylene or alkenylene group having from 1 to 6 carbon atoms and each optionally being substituted by from 1 to 4 alkyl groups each having from 1 to 3 carbon atoms;
- $R^b$ and $R^c$ represents an alkylene or alkenylene group having 3 or 4 carbon atoms in a straight chain, each being optionally substituted by a 1 or 2 alkyl groups each having from 1 to 3 carbon atoms, the total number of carbon atoms in said straight chains of $R^b$ and $R^c$ being 7;
- $R^2$ and $R^3$ are the same as or different from each other and each represents a hydrogen atom, or a group of formula R, RCO—, ROCO—, or RNHCO—, where
  - R represents a lower alkyl group or an aryl group, said alkyl or aryl group being optionally substituted by one or more of the substituents α, defined below;
- the chiral carbon atom indicated by the asterisk is in the L configuration;
- Z is an aromatic amino acid residue;
- n is 0 or 1;
- $R^1$ represents a hydrogen atom or a lower alkyl group or an aryl group, said alkyl or aryl group being optionally substituted by one or more of the substituents α, defined below;
- W represents a hydrogen atom or an alkyl or aryl group; and
- substituents α are selected from: halogen atoms, amino groups, alkylamino groups, dialkylamino groups, cyano groups, hydroxy groups, alkyl groups (except when the substituted group is alkyl), aryl groups, carbamoyl groups, alkylcarbamoyl groups, dialkylcarbamoyl groups and carboxy groups and esters thereof;
and pharmaceutically acceptable salts thereof.

2. A compound according to claim 1, having the formula (Ia):

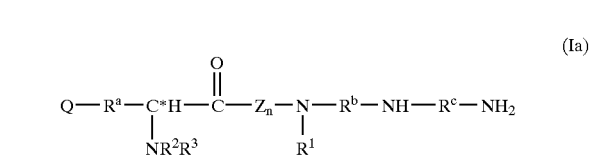
(Ia)

wherein Q, $R^a$, $R^b$, $R^c$, $R^2$, $R^3$, Z, n, and $R^1$ are as in claim 1.

3. A compound according to claim 1, having the formula (Ib):

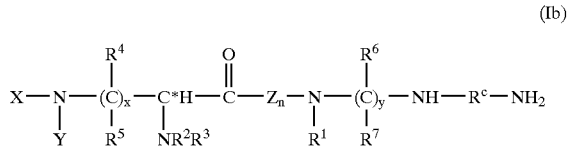
(Ib)

wherein:
- X, Y, Z, n and $R^1$ are as defined in claim 1;
- X is an integer from 1 to 5;
- Y is 3 or 4
- $R^4$, $R^5$, $R^6$ and $R^7$ may be the same or different and each represents a hydrogen atom or a lower alkyl group; and
- the chiral carbon atom indicated by the asterisk is in the L configuration.

4. Compounds according to claim 1, in which Z represents an aromatic amino acid residue in the L configuration.

5. A compound according to claim 1 which is:

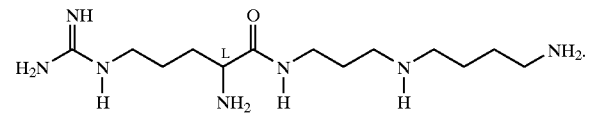

6. A compound according to claim 1 which is:

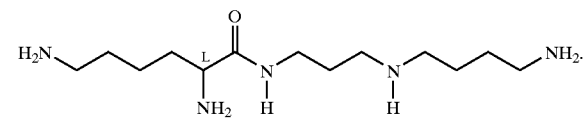

7. A compound according to claim 1 which is:

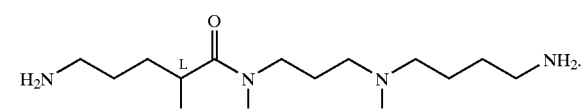

8. A compound according to claim 1 which is:

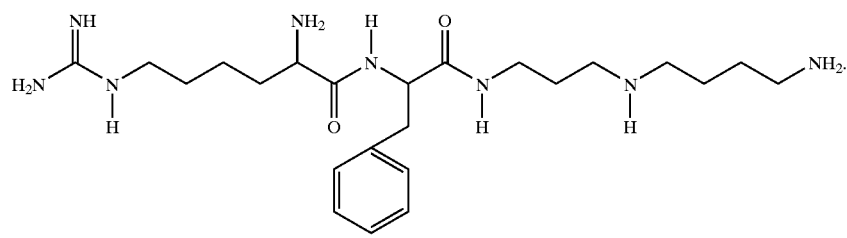

9. A compound according to claim 1 which is:
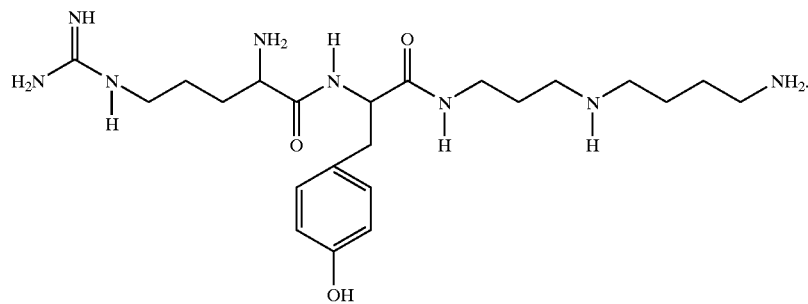
10. A compound according to claim 1 which is:
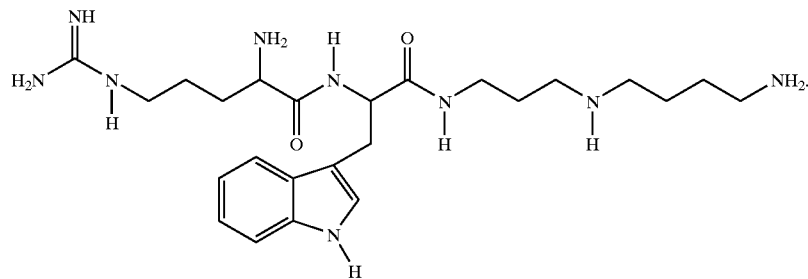
11. A compound according to claim 1 which is:
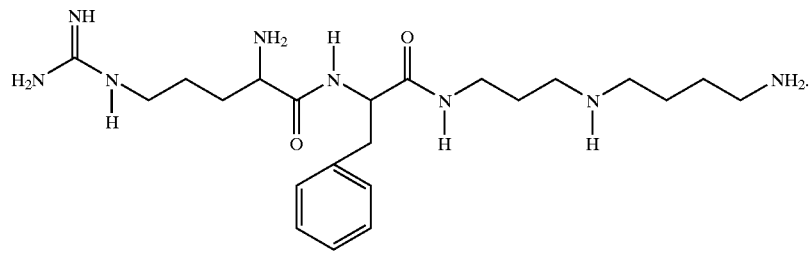
12. A compound according to claim 1 which is:
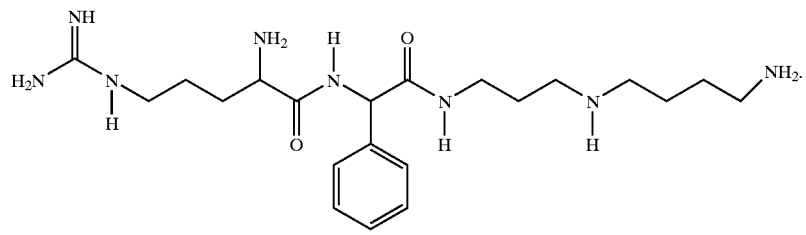
13. A compound according to claim 1 which is:
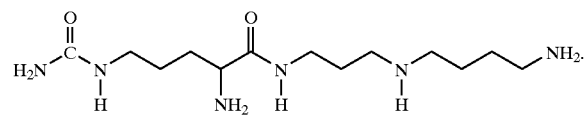
* * * * *